US010413959B2

(12) United States Patent
Brown

(10) Patent No.: US 10,413,959 B2
(45) Date of Patent: Sep. 17, 2019

(54) APPARATUS AND METHOD FOR CRIMPING COUPLING RINGS

(71) Applicant: Vincent Brown, Mobile, AL (US)

(72) Inventor: Vincent Brown, Mobile, AL (US)

( * ) Notice: Subject to any disclaimer, the term of this patent is extended or adjusted under 35 U.S.C. 154(b) by 89 days.

(21) Appl. No.: 15/650,534

(22) Filed: Jul. 14, 2017

(65) Prior Publication Data
US 2018/0015526 A1 Jan. 18, 2018

Related U.S. Application Data

(60) Provisional application No. 62/362,484, filed on Jul. 14, 2016.

(51) Int. Cl.
| | |
|---|---|
| *B21D 41/00* | (2006.01) |
| *B21D 39/04* | (2006.01) |
| *A61M 39/28* | (2006.01) |
| *B21D 5/02* | (2006.01) |
| *A62C 33/04* | (2006.01) |
| *F16K 7/06* | (2006.01) |
| *B25B 27/10* | (2006.01) |
| *F16L 37/084* | (2006.01) |

(52) U.S. Cl.
CPC ......... *B21D 39/046* (2013.01); *A61M 39/283* (2013.01); *A62C 33/04* (2013.01); *B21D 5/0209* (2013.01); *B21D 39/048* (2013.01); *B21D 41/00* (2013.01); *B25B 27/10* (2013.01); *F16K 7/061* (2013.01); *F16L 37/0844* (2013.01)

(58) Field of Classification Search
CPC .... B21D 41/00; B21D 5/0209; B21D 39/046; B21D 39/048; F16K 7/061; A61M 39/283; A62C 33/04; B25B 27/10

USPC ............................................... 72/402
See application file for complete search history.

(56) References Cited

U.S. PATENT DOCUMENTS

| | | | | | |
|---|---|---|---|---|---|
| 2,841,358 | A | * | 7/1958 | Russell | A61M 39/283 |
| | | | | | 251/8 |
| 2,865,591 | A | * | 12/1958 | Holinshead | A61M 39/283 |
| | | | | | 24/135 N |
| 2,917,956 | A | * | 12/1959 | Merion | B21D 5/0209 |
| | | | | | 254/DIG. 8 |
| 3,117,615 | A | * | 1/1964 | Graven | B21D 41/00 |
| | | | | | 251/8 |
| 3,589,668 | A | * | 6/1971 | Gill | F16K 7/061 |
| | | | | | 24/525 |
| 3,730,478 | A | * | 5/1973 | Burke | F16K 7/061 |
| | | | | | 251/8 |

(Continued)

*Primary Examiner* — David B Jones
(74) *Attorney, Agent, or Firm* — ADAMSIP, LLC; James Hunter Adams; Stephen Thompson

(57) ABSTRACT

An apparatus and method for crimping coupling rings are provided. The apparatus generally has a lower clamp head and an upper clamp head that may be drawn together by a fastener. The lower and upper clamp heads are designed to receive a first portion and a second portion of a coupling ring, respectively. A first and second post holds the clamp heads adjacent to each other. The upper clamp head is secured to the first post such that the upper clamp head may rotate in a generally circular motion to switch the apparatus from a closed to an open configuration, or vice versa. When the apparatus is placed in a closed configuration, the fastener may be engaged to draw the clamp heads together to increase the compressive force imposed on a coupling ring until the coupling ring becomes crimped.

18 Claims, 8 Drawing Sheets

(56) References Cited

U.S. PATENT DOCUMENTS

| | | | | |
|---|---|---|---|---|
| 4,978,100 A | * | 12/1990 | Peurifoy | A62C 33/04 251/8 |
| 5,257,525 A | * | 11/1993 | Clarke | B21D 39/046 29/237 |
| 5,353,623 A | * | 10/1994 | Bobenhausen | B21D 39/048 29/237 |
| 6,866,241 B1 | * | 3/2005 | Libretto | F16K 7/061 251/7 |
| 8,177,187 B2 | * | 5/2012 | Feast | F16K 7/061 251/7 |

* cited by examiner

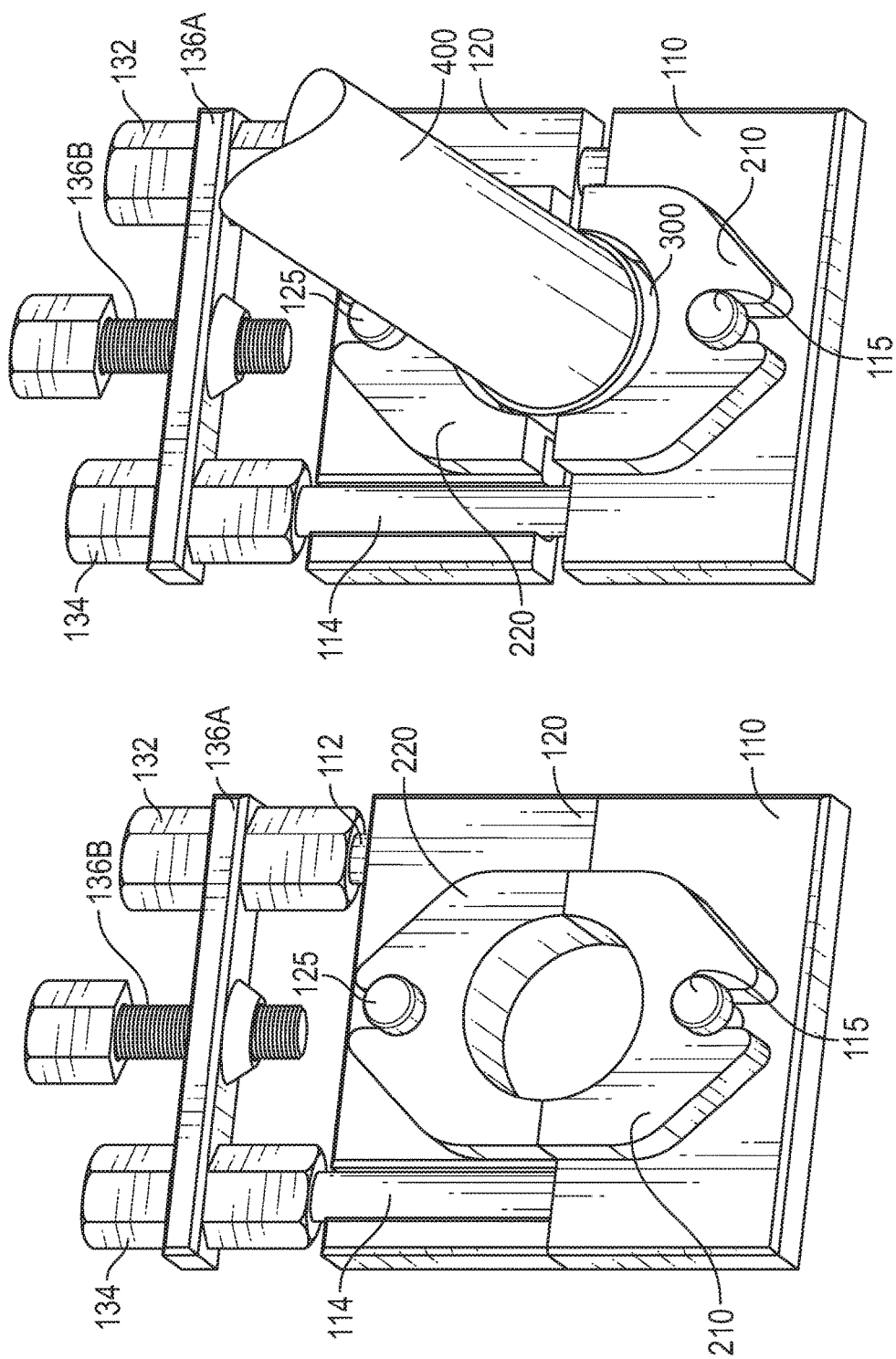

APPARATUS AND METHOD FOR CRIMPING COUPLING RINGS

CROSS-REFERENCE TO RELATED APPLICATIONS

This application claims priority to U.S. Provisional Patent Application No. 62/362,484 entitled "Swing Gate Flexible Piping Clamper," filed Jul. 14, 2016, which application is incorporated herein in its entirety by reference.

FIELD OF THE DISCLOSURE

The subject matter of the present disclosure refers generally to an apparatus and method for crimping coupling rings.

BACKGROUND

Flexible piping (e.g., polybutylene, chlorinated polyvinyl chloride, cross linked polyethylene, etc.) is commonly used to facilitate the transportation of fluids such as water, oil, and gas from one area to another. Such piping is generally elongated and manufactured to have standardized diameters, such as three-eighths inch, one-half inch, five-eighths inch, and one inch. Many applications require inflowing fluids to be diverted in several different directions or to several different areas, thus requiring a plurality of pipes to be coupled together to create a manifold. Accordingly, many applications require the flexible piping to be cut into different sectional parts and subsequently joined together using pipe fittings, such as metal insert fittings or tee fittings. A common procedure for coupling flexible pipes to pipe fittings involves inserting an end of a pipe fitting into an opening of a flexible pipe, placing a coupling ring around the flexible pipe at a location above the pipe fitting, and subsequently crimping the coupling ring to deform it, thereby securing the pipe to the pipe fitting.

Traditional crimping tools generally comprise a pair of clamp heads, a pair of clamping jaws within the respective clamp heads, and a pair of handles for drawing the heads together. The clamp heads and clamping jaws generally define the crimping portion of such crimping tools. Such traditional crimping tools generally work by drawing the clamp heads of the tool toward one another using leverage from the handles in order to compress the coupling around its entire circumference. In recent years, power-crimping tools have been developed which utilize an electric motor, instead of handles, to draw the clamp heads towards one another. The compressive force imposed on the coupling ring by the clamping jaws as the clamp heads draw together causes the coupling ring to compress inwards.

However, known traditional crimping tools and power-crimping tools alike are generally bulky and cumbersome to use due to the handles or electric motor element extending outward from the crimping section of the tool. In many applications, flexible piping is situated within tight working spaces that spatially prohibit the use of known crimping tools unless the working space is significantly modified. Moreover, such flexible piping is frequently utilized in applications such as indoor plumbing, where the flexible piping, pipe fittings, and corresponding coupling rings are located behind walls, ceilings, or floors. Accordingly, repairs to failed piping elements using known crimping tools often require the removal of large sections of walling, ceiling, flooring, and/or support studs to provide sufficient space for the crimping tool to function. Thus, the design of known crimping often increases the amount of work, time, and cost needed to install or repair piping.

Accordingly, there is a need in the art for a crimping apparatus capable of working in tight spaces. Moreover, a need exists for a crimping apparatus that reduces the amount of walling, ceiling, flooring, and/or support studs that must be removed in order to crimp a coupling ring located behind a wall, ceiling, or floor. Additionally, a need exists in the art for a method for crimping coupling rings using such an apparatus.

SUMMARY

An apparatus and method for crimping coupling rings are provided. The crimping apparatus comprises a lower clamp head configured to receive a first portion of a coupling ring and an upper clamp head configured to receive a second portion of a coupling ring. The lower and upper clamp heads are held adjacent via a first post and a second post. In one preferred embodiment, the lower clamp head is removably secured to the first post and the second post such that the lower clamp head can slide thereupon when the apparatus is in a non-crimped configuration. In another embodiment, the first and second post may be fixedly attached in parallel and extending outward from the top of the lower clamp head. The upper clamp head is rotably secured to the first post such that the upper clamp head may rotate in a substantially circular motion about the first post. The upper clamp head also has an indentation configured to receive the second post therein. By rotating the upper head clamp about the first post, a user can switch the apparatus from an open configuration to a closed configuration, or vice versa. In an open configuration, the second post is absent from the indentation and the lower and upper clamp heads are unaligned. In a closed configuration, the second post rests within the indentation and the lower and upper clamp heads are aligned. Thus, by rotating the upper clamp head, the apparatus can be placed around a coupling ring or removed from a coupling ring.

The apparatus further comprises a fastener configured to draw the upper clamp head towards the lower clamp head in order to crimp a coupling ring disposed between the two clamp heads. As the upper clamp head draws closer to the lower clamp head, the compressive force imposed on the coupling ring increases, thereby causing the coupling ring to become crimped. To reduce the spatial dimensions of the apparatus while still enabling the apparatus to effectively crimp coupling rings, the fastener is designed to draw the upper clamp head towards the lower clamp head as torque is applied thereto in a defined, tightening motion. By engaging the fastener, a user can incrementally increase the force applied to the upper clamp head by hand or by tool to gradually crimp a coupling ring. In this way, the crimping apparatus generates the required crimping force to crimp a coupling ring, thereby alleviating the need for bulky handles or electrical motors, as currently used within the art. In turn, by alleviating the need for such bulky handles or electrical motors, the apparatus can function in tight working spaces and thus reduces the amount of walling, ceiling, flooring, and/or support studs that may be required to be removed in order to crimp coupling rings located behind such structures.

In one preferred embodiment, the fastener is a tightening bar comprising a bar secured to the first post and to the second post and a bolt extending through a threaded opening that extends transversely through the bar. As the bolt is threaded through the opening in the bar, it presses against the upper clamp head, thereby drawing the upper clamp head toward the lower clamp head. In another embodiment, the first and second post each have a proximal end and a threaded distal end, and the fastener comprises a first nut and second nut having threading compatible with the threaded distal end of the first and second post, respectively. In such embodiments, the upper clamp head is drawn towards the lower clamp head by screwing the first nut and second nut towards the proximal end of the first post and second post, respectively. To accommodate the generally circular design of most coupling rings, the upper clamp head and lower clamp head may each have a semicircular arch therein such that a circular opening is formed when the clamp heads are aligned and in contact. In a preferred embodiment, the apparatus may further comprise an insert that serves to decrease the diameter of the opening formed by the two clamp heads in order to accommodate smaller coupling rings.

To use the apparatus, the lower clamp head is first positioned around a first portion of a coupling ring. The upper clamp head is then rotated about the first post until the indentation of the upper clamp head receives the second post therein, thereby placing the apparatus in a closed position. The fastener is then engaged to draw the upper clamp head toward the lower clamp head until the upper clamp head and lower clamp head contact one another and the coupling ring is crimped.

The foregoing summary has outlined some features of the apparatus and methods of the present disclosure so that those skilled in the pertinent art may better understand the detailed description that follows. Additional features that form the subject of the claims will be described hereinafter. Those skilled in the pertinent art should appreciate that they can readily utilize these features for designing or modifying other structures for carrying out the same purposes of the device and methods disclosed herein. Those skilled in the pertinent art should also realize that such equivalent designs or modifications do not depart from the scope of the device and methods of the present disclosure.

DESCRIPTION OF THE DRAWINGS

These and other features, aspects, and advantages of the present disclosure will become better understood with regard to the following description, appended claims, and accompanying drawings where:

FIG. 14 shows a perspective view of an apparatus embodying features consistent with the principles of the present disclosure.

FIG. 15 shows a perspective view of an apparatus embodying features consistent with the principles of the present disclosure being used to crimp a coupling ring to a pipe.

DETAILED DESCRIPTION

Figure 1:
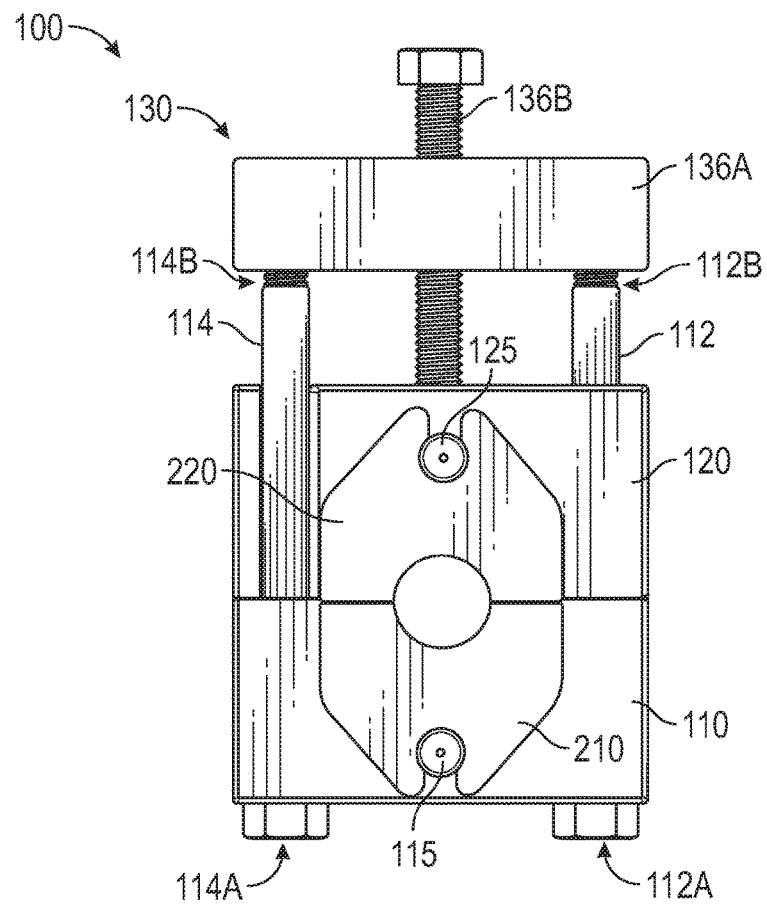
FIG. 1 shows a front elevational view of an apparatus embodying features consistent with the principles of the present disclosure.

In the Summary above and in this Detailed Description, and the claims below, and in the accompanying drawings, reference is made to particular features, including method steps, of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with/or in the context of other particular aspects of the embodiments of the invention, and in the invention generally.

The term "comprises" and grammatical equivalents thereof are used herein to mean that other components, steps, etc. are optionally present. For example, a system "comprising" components A, B, and C can contain only components A, B, and C, or can contain not only components A, B, and C, but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "removably secured" and grammatical equivalents thereof are used herein to mean the joining of two components in a manner such that the two components are secured together, but may be detached from one another and re-secured together without requiring the use of specialized tools. As used herein, "a defined, tightening motion" and grammatical equivalents thereof are used to refer to a rotating motion, which is preferably a clockwise motion, of a fastener.

Turning now to the drawings FIGS. 1-15 illustrate preferred embodiments of an apparatus, or various components thereof, for crimping coupling rings. The apparatus 100 is generally designed to provide a compact crimping tool that reduces the amount of walling, ceiling, flooring, and/or support studs that must be removed in order to install or repair a coupling ring in an obstructed area. The apparatus 100 has a lower clamp head 110 configured to receive a first portion of a coupling ring 300 therein and an upper clamp head 120 configured to receive a second portion of the coupling ring 300 therein. The apparatus 100 also has a first post 112 and a second post 114, which serve to keep the lower clamp head 110 and upper clamp head 120 adjacent to each other and provide a guide on which the lower and/or upper clamp heads 110, 120 may slide upon. In a preferred embodiment, the lower clamp head 110 has a first and second bore therein, which serve to removably secure the lower clamp head 110 when the first and second post 112, 114 are inserted therethrough. In another preferred embodiment, the first post 112 and the second post 114 may be fixedly attached in parallel and extend outward from a top side 110B of the lower clamp head 110. The upper clamp head 120 is rotably secured to the first post 112 such that the upper clamp head 120 may rotate about the first post 112 in a generally circular motion to switch the apparatus 100 from an open to a closed configuration, or vice versa.

The apparatus further comprises a fastener 130 configured to draw the upper clamp head 120 toward the lower clamp head 110. Once the lower clamp head 110 receives the first portion of the coupling ring 300 and the apparatus 100 is placed in a closed configuration, the fastener 130 may be engaged to draw the upper clamp head 120 towards the lower clamp head 110. By applying torque to the fastener 130 in a defined, tightening motion, a user can incrementally increase the compressive force imposed on the coupling ring 300 until the coupling ring 300 is crimped. In this way, the apparatus 100 may be used to crimp a coupling ring 300 to secure a pipe 400 to a pipe fitting.

The term "closed configuration" and grammatical equivalents thereof are used herein to mean that the apparatus is in a configuration wherein the second post rests within the indentation of the upper clamp head, and the upper and lower clamp heads are aligned. A closed configuration is utilized to position the apparatus around a coupling ring. The term "open configuration" and grammatical equivalents thereof are used herein to mean that the apparatus is in a configuration wherein the second post does not rest within the indentation of the upper clamp head, and the upper and lower clamp heads are not aligned. An open configuration is utilized for placing the apparatus around a coupling ring or for removing the apparatus from a coupling ring. The termed "crimped configuration" and grammatical equivalents thereof are used herein to indicate that the apparatus is in a closed configuration and the upper and lower clamp heads are applying compressive forces to a coupling ring. In a crimped configuration, the bottom side of the upper clamp head is generally in contact with, or in close proximity to, the top side of the lower clamp head.

Figure 2:
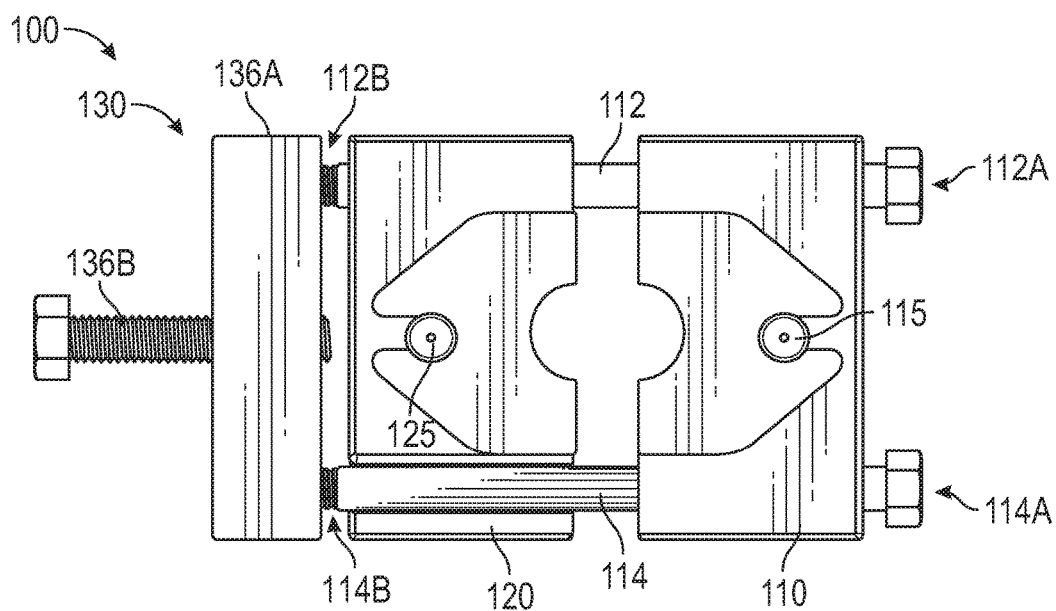
FIG. 2 shows a front elevational view of an apparatus embodying features consistent with the principles of the present disclosure.
Figure 3:
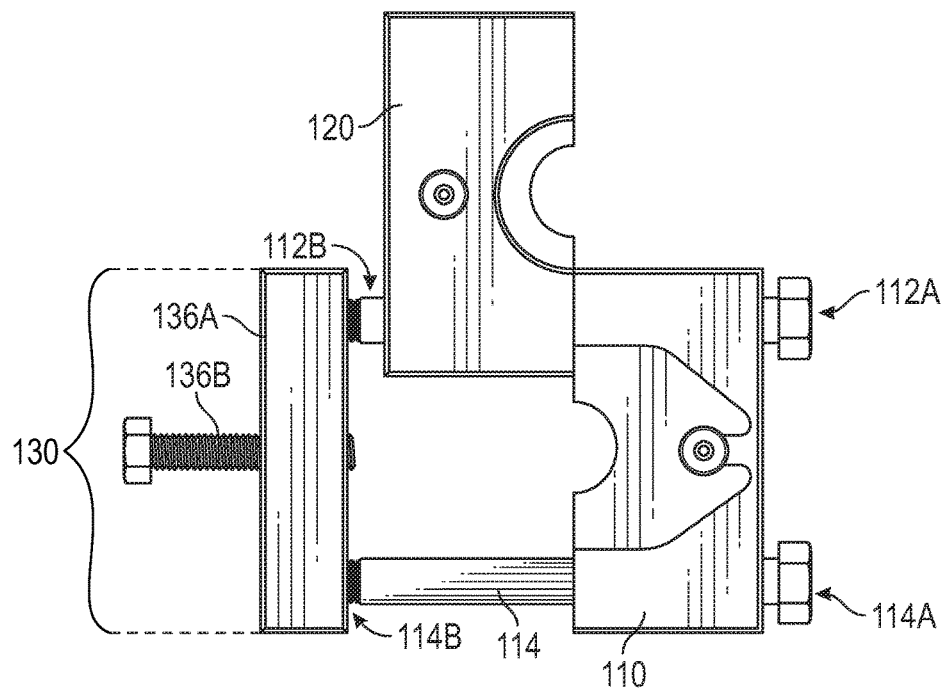
FIG. 3 shows a rear elevational view of an apparatus embodying features consistent with principles of the present disclosure.
Figure 4:
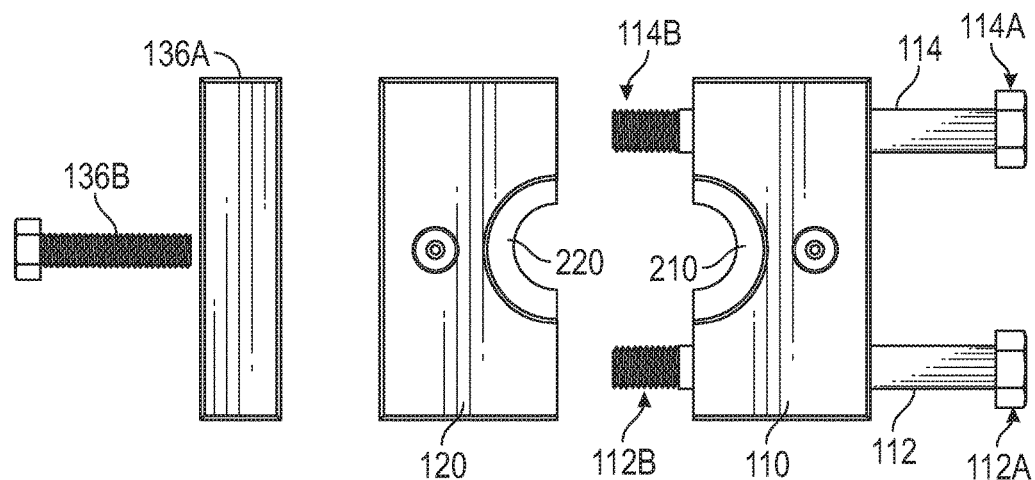
FIG. 4 shows a partially exploded view of an apparatus embodying features consistent with the principles of the present disclosure.
Figure 5:
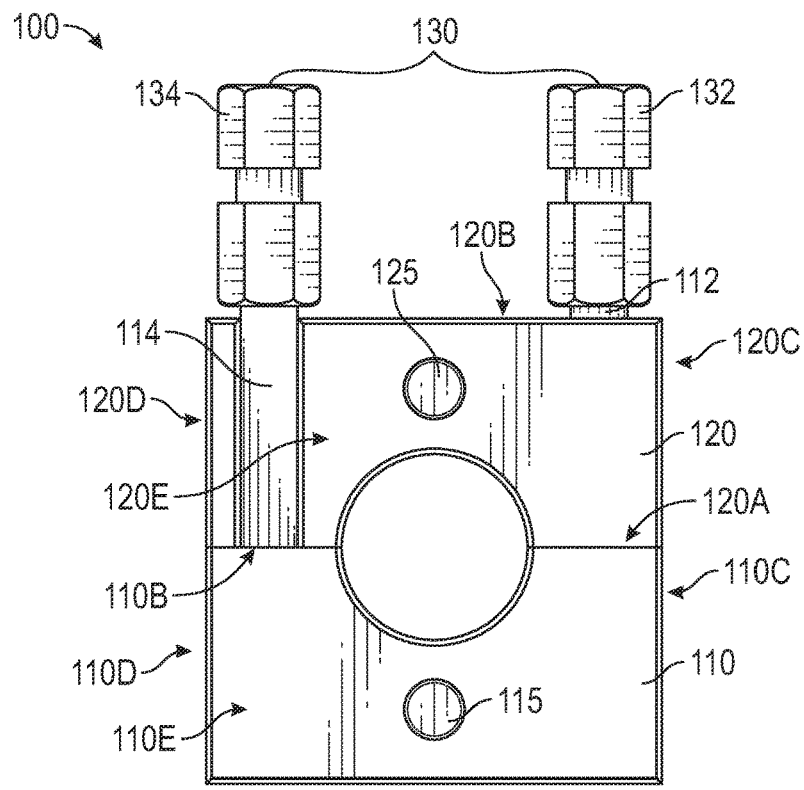
FIG. 5 shows a front elevational view of an apparatus embodying features consistent with the principles of the present disclosure.

As shown in FIGS. 1-7 and 11-15, the apparatus 100 comprises a lower clamp head 110, a first post 112, a second post 114, an upper clamp head 120 rotably secured to the first post 112 and having an indentation therein 122, and a fastener 130. As shown in FIGS. 1-4 and 13, the first post 112 has a proximal end 112A and a distal end 112B. Similarly, the second post 114 has a proximal end 114A and a distal end 114B. As best shown in FIGS. 5-7 and 13, the lower clamp head 110 is defined by a bottom side 110A, a top side 110B, a hinge side 110C, a latch side 110D, a front face 110E, and a back face 110F. In a preferred embodiment, the lower clamp head 110 has a first bore and a second bore that is parallel to the first bore therein (not shown). The diameter of the first and second bore of the lower clamp head 110 is at least slightly greater than the diameter of the first post 112 and the second post 114, respectively. The first and second bore of the lower clamp head 110 extend from the bottom side 110A to the top side 110B of the lower clamp head such that the first and second bore each have an opening at the bottom side 110A and the top side 110B of the lower clamp head 110. The lower clamp head 110 may be removably secured to the first post 112 by inserting the distal end 112B of the first post 112 through the first bore of the lower clamp head and inserting the distal end 114B of the second post 114 through the second bore of the lower clamp head, as shown in FIG. 4. In such embodiments, the first and second post 112, 114 are of a sufficient length such that when the apparatus 100 is fully assembled the lower and upper clamp heads 110, 120 may slide upon the first and second post 112, 114 when the apparatus 100 is in a non-crimped configuration, as best shown in FIG. 2. As shown in FIGS. 1-4, the proximal end 112A of the first post 112 and the proximal end 114B of the second post 114 may be enlarged to prevent the lower clamp head 110 from sliding off while the apparatus 100 is in use. To provide a better griping surface for hand or tool, the proximal ends 112A, 114A of the first post and second post 112, 114, respectively, may have a multi-faced head.

Figure 12:
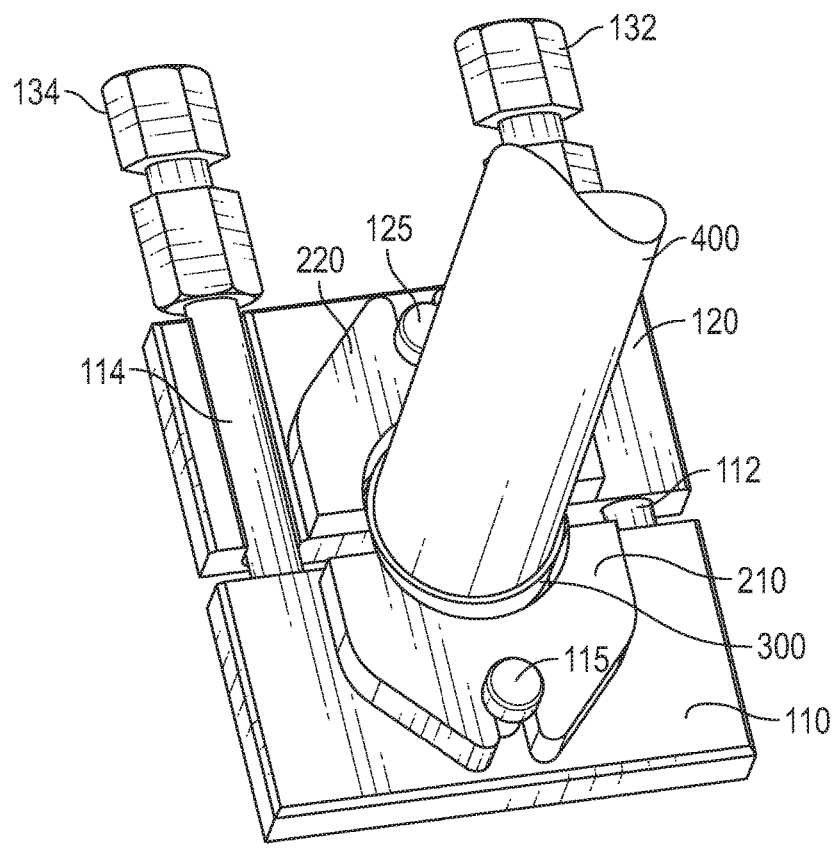
FIG. 12 shows a perspective view of an apparatus embodying features consistent with the principles of the present disclosure being used to crimp a coupling ring to a pipe.
Figure 13:
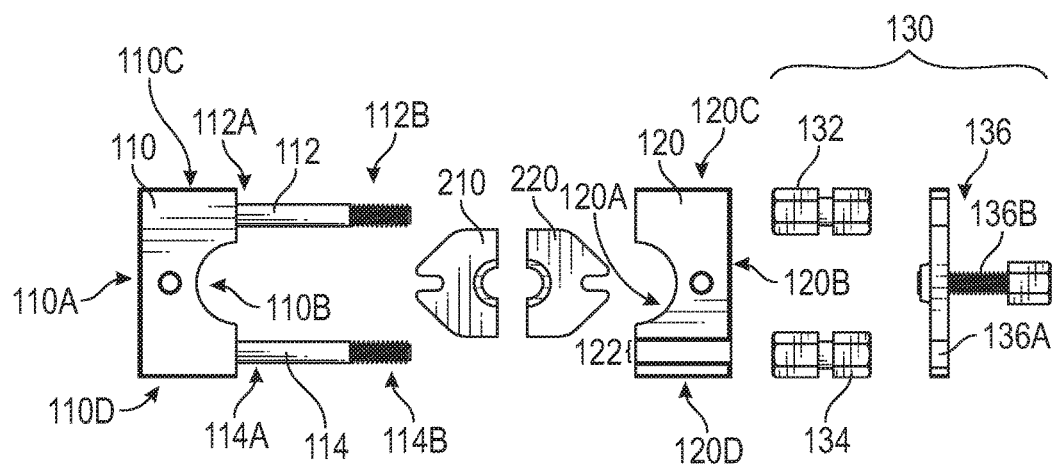
FIG. 13 shows an exploded view of an apparatus and insert embodying features consistent with the principles of the present disclosure.

In another embodiment, instead of extending through the lower clamp head 110 from the bottom side 110A to the top side 110B, the first post 112 and second post 114 may be fixedly attached to the top side 110B of the lower clamp head 110, as best shown in FIGS. 5-7 and 11-15. In such embodiments, the first post 112 and the second post 114 are preferably positioned opposite one another and in parallel, and preferably extend outwardly from the top side 110B of the lower clamp head 110. In a preferred embodiment, the first post 112 extends outwardly from the top side 110B at a point substantially near the hinge side 110C, and the second post 114 extends outwardly from the topside 110B at a point substantially near the latch side 110D. The first post 112 and the second post 114 have a length greater than the hinge side 120C and latch side 120D, respectively, of the upper clamp head 120. The first post 112 and the second post 114 are preferably cylindrical rods, though other suitable elongated members may be used as the first and second post. The proximal end 112A of the first post 112 and the proximal end 114A of the second post 114 may be permanently secured to the top side 110B of the lower clamp head 110 such that the lower clamp head 110, first post 112, and second post 114 form a unitary component, as best shown in FIG. 13. Alternatively, the proximal end 112A of the first post 112 and the proximal end 114A of the second post 114 may be removably secured to the top side 110B of the lower clamp head 110.

As with the lower clamp head 110, the upper clamp head 120 is also defined by a bottom side 120A, a top side 120B, a hinge side 120C, a latch side 120D, a front face 120E, and a back face 120F. As shown best in FIGS. 12 and 15, the lower clamp head 110 is configured to receive a first portion of a coupling ring 300, and the upper clamp head 120 is configured to receive a second portion of the coupling ring 300 therein. To accommodate the generally circular design of most coupling rings, the top side 110B of the lower clamp head 110 and the bottom side 120A of the upper clamp head 120 preferably have a semicircular arch therein, as shown best in FIG. 2. In a preferred embodiment, the semicircular arch of each clamp head 110 and 120 is disposed between the first post 112 and the second post 114 when the apparatus 100 is in a closed configuration, as shown in FIGS. 1, 7, 11-12, and 14-15. When the apparatus 100 is in a closed configuration and the clamp heads 110, 120 are drawn together such that the apparatus 100 retains a crimped configuration, the semicircular arches of the clamp heads 110, 120 form a circular opening within the apparatus 100. In a preferred embodiment, the circular opening formed within the apparatus 100 by the upper clamp head 120 and lower clamp head 110 has a diameter equal to one inch. However, one of skill in the art will appreciate that the circular opening may have a diameter of any suitable size including, but not limited to, three-quarters inch, five-eights inch, half inch, or three-eights inch. Additionally, one of skill in the art will appreciate that the lower clamp head 110 and the upper clamp head 120 may be shaped to accommodate coupling rings 300 of any shape without departing from the inventive subject matter disclosed herein.

Figure 7:
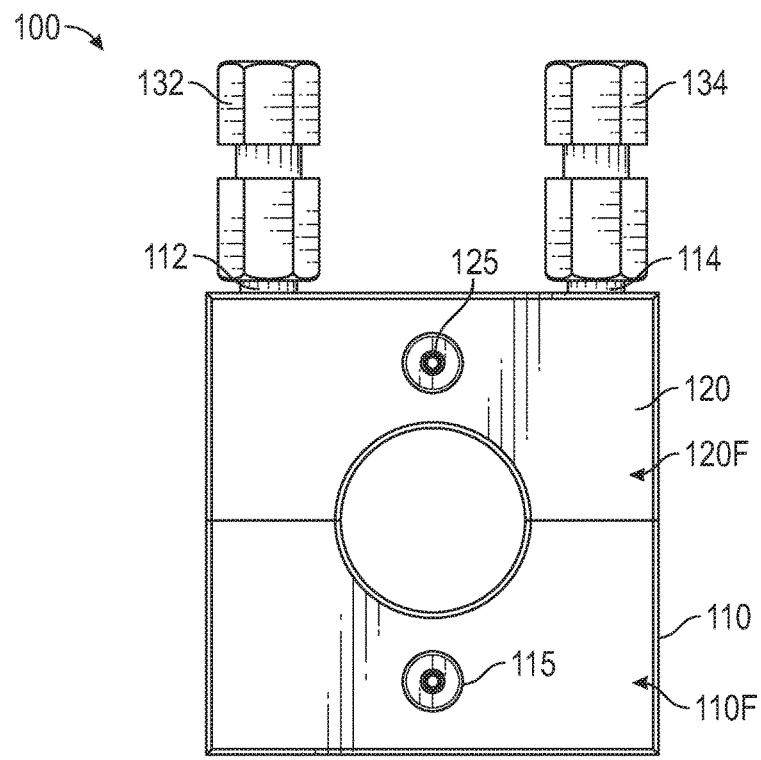
FIG. 7 shows a rear elevational view of an apparatus embodying features consistent with the principles of the present disclosure.
Figure 8:
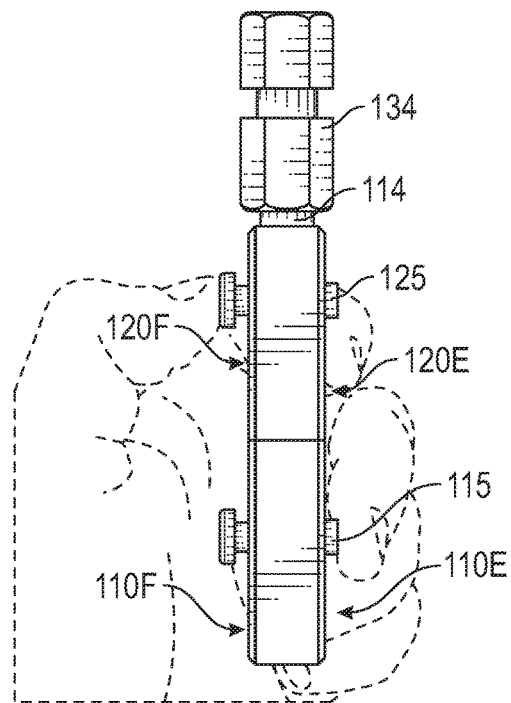
FIG. 8 shows a side elevational view of an apparatus embodying features consistent with the principles of the present disclosure.

In a preferred embodiment, the lower clamp head 110 and the upper clamp head 120 may each have a generally rectangular exterior shape such that when the apparatus 100 is placed in a crimped configuration the clamp heads 110, 120 in combination form a square, as seen in FIG. 7. It is understood, however, that the lower clamp head 110 and upper clamp head 120 may have different exterior shapes without departing from the inventive subject matter disclosed herein.

Figure 6:
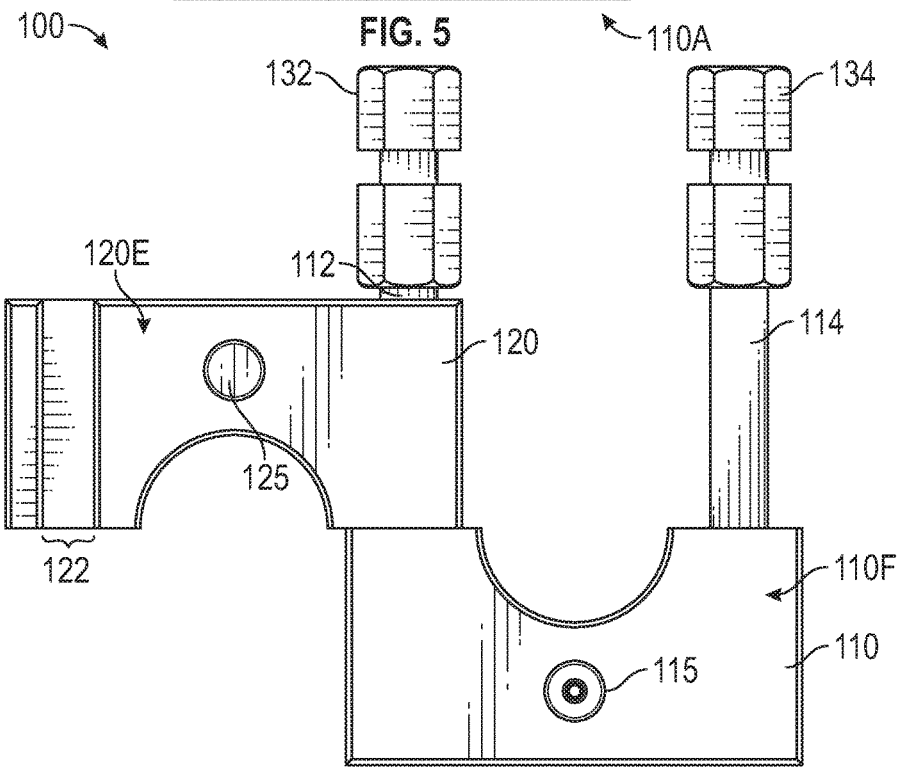
FIG. 6 shows an elevational view of an apparatus embodying features consistent with the principles of the present disclosure.

As shown best in FIGS. 3 and 6, the upper clamp head 120 is rotably secured to the first post 112 such that the upper clamp head 120 may swing in a substantially circular motion about the first post 112. In a preferred embodiment, the upper clamp head 120 is rotably secured to the first post 112 via a bore (not shown). The bore extends from the bottom side 120A to the top side 120B at a point substantially near the hinge side 120C of the upper clamp head 120 such that the bore has an opening at the bottom side 120A and at the top side 120B of the upper clamp head 120. In such embodiments, the upper clamp head 120 is rotably secured to the first post 112 by inserting the first post 112 through the bore. To enable the upper clamp head 120 to rotably secure to the first post 112, the diameter of the bore is at least slightly greater than the diameter of the first post 112. Alternatively, the upper clamp head 120 may be rotably secured to the first post 120 by any suitable external instrument or device, such as a hinge having a knuckle with a diameter greater than the diameter of the first post 112.

Once rotably secured to the first post 112, the upper clamp head 120 may rotate about the first post in a substantially circular motion until the latch side 120D of the upper clamp head reaches the second post 114. To facilitate flush alignment of the lower clamp head 110 and the upper clamp head 120, the front face 120E of the upper clamp head 120 has an indentation 122 therein extending from the bottom side 120A to the top side 120B at a point substantially near the latch side 120D. The dimensions of the indentation 122 are preferably such that when the front face 120E of the upper clamp head 120 contacts the second post 114, the second post 114 rests flush with the front face 120E of the upper clamp head 120. The force applied by the fastener 130 to the upper clamp head 120, as detailed below, may serve to ensure the second post 114 does not become dislodged from the indentation 122 while crimping a coupling ring 300. In some instances, the indentation 122 and/or the second post 114 may have an instrument or device therein or secured thereto configured to removably secure the second post 114 within the indentation 122. For instance, magnets may be disposed within the indentation 122 and/or second post 114.

By rotating the upper clamp head 120 about the first post 112, a user can switch the apparatus 100 from an open configuration to a closed configuration, or vice versa. In a closed configuration, the upper clamp head 120 is rotated such that the second post 114 rests within the indentation 122 and the upper clamp head and lower clamp head are aligned, as shown in FIGS. 1, 7-9, 11-12, and 14-15. As shown best in FIGS. 12 and 15, the apparatus 100 is placed in a closed configuration prior to crimping a coupling ring 300. In an open configuration, the upper clamp head 120 is rotated such that the second post 114 is removed from the indentation 122 and the upper clamp head 120 and lower clamp head 110 are unaligned, as shown best in FIGS. 3 and 6.

To position the apparatus 100 around a coupling ring 300, the apparatus 100 is preferably first placed in an open configuration, and the lower clamp head 110 is positioned around a first portion of the coupling ring 300. The upper clamp head 120 is then rotated about the first post 112 until the apparatus 100 is in a closed configuration. Depending on the orientation of the apparatus 100 and positioning of the upper clamp head 120 on the first and second posts 112, 114, a user may be required to slide the upper clamp head 120 towards the distal end 112B of the first post 112. This may be required to allow the upper clamp head 120 enough space to clear the coupling ring 300 and the pipe 400 around which the coupling ring is positioned when rotating the upper clamp head 120 into a closed configuration. Once the apparatus 100 is in a closed configuration, the upper clamp head 120 may be positioned such that a second portion of the coupling ring 300 is received by the upper clamp head 120, as best shown in FIGS. 12 and 15.

Alternatively, both the lower clamp head 110 and upper clamp head 120 may be positioned around the coupling ring 300 while the apparatus 100 is in a closed configuration. In such embodiments, the apparatus 100 may be positioned around the coupling ring 300 by sliding the upper clamp head 120, on the first post 112 and the second post 114, away from the lower clamp head 110 until enough space exists for the coupling ring 300 and pipe 400 to be placed between the clamp heads 110, 120. In certain embodiments disclosed herein, the apparatus 100 may alternatively be positioned around the coupling ring 300 by sliding the lower clamp head 110, on the first post 112 and the second post 114, away from the upper clamp head 120 unit until enough space exists for the coupling ring 300 and pipe 400. To provide more or less room for the lower clamp head 110 and/or upper clamp head 120 to slide on the first and second posts 112, 114, the fastener 130 may be loosened or tightened, respectively.

The fastener 130 is generally designed such that a user can incrementally increase the extent to which the upper clamp head 120 is drawn towards the lower clamp head 110 by engaging the fastener 130. In a preferred embodiment, the fastener 130 comprises nuts or bolts that may be rotated clockwise to force the upper clamp head 120 toward the lower clamp head 110. Conversely, the nuts or bolts of the fastener 130 may be rotated counterclockwise to release the upper clamp head 120. However, one of skill in the art will appreciate the direction or motion of rotation may be reversed or altered without departing from the inventive subject matter disclosed herein.

By applying torque to the nuts or bolts of the fastener 130 in a defined, tightening motion, a user can incrementally increase the pressure applied to a coupling ring 300 positioned between the upper clamp head 120 and the lower clamp head 110 to gradually crimp the coupling ring 300. In this way, the apparatus 100 of the present disclosure alleviates the need for the use of bulky handles or electrical motors to generate the required crimping force, as currently used within the art. Thus, the apparatus 100 of the present disclosure provides a functional crimping tool that is smaller than those currently known within the art. In turn, the apparatus 100 of the present disclosure effectively reduces the amount of walling, ceiling, flooring, and/or support studs that must be removed in order to crimp coupling rings positioned behind such structures. Torque may be applied to fastener 130 components by hand, by tool, or by using a combination thereof. To ensure enough force is applied to crimp the coupling ring 300, the use of a tightening tool, such as a wrench or ratchet, may be generally preferred.

In one preferred embodiment, the fastener 130 may be a tightening bar 136 comprising a bar 136A, which is secured to the first and second post 112, 114, and a bolt 136B. The bar 136A may be removably or permanently secured to the first post 112 and to the second post 114. In a preferred embodiment, the bar 136A of the tightening bar 136 has a first end configured to removably secure to the first post 112 and a second end configured to removably secure to the second post 114. In one such embodiment, the first end of the bar 136A has a first bore therein (not shown) and the second end of the bar 136A has a second bore therein (not shown). In such embodiments, the distal end 112B of the first post 112 and the distal end 114B of the second post 114 are preferably threaded. To interlock the bar 136A to the first and second post 112, 114, the first bore of the bar 136A has threading compatible with the distal end 112B of the first post 112 such that the distal end 112B of the first post 112 can be screwed into the first bore, as shown best in FIGS. 1-3. Similarly, the second bore of the bar 136A has threading compatible with the distal end 114B of the second post 114 such that the distal end 114 of the second post 114 can be screwed into the second bore. To prevent the distal ends of the posts from being threaded entirely through the bar 136A, the first and second bore may only partially extend through the bar 136A, such that each bore only has a single opening within the bar 136A. Alternatively the first and second bore may extend entirely through the bar 136A, such that each bore has two openings within the bar 136A and the distal ends of the posts can be threaded entirely through the bar 136A.

As best shown in FIG. 4, by unscrewing the distal end 112B of the first post 112 and the distal end 114B of the second post 114 from the first and second bore of the bar 136A, respectively, the apparatus can be disassembled such that the lower clamp head 110, the upper clamp head 120, the first post 112, the second post 114, and the tightening bar 136 are separate and apart from one another. Depending on user preference, the apparatus 100 may be disassembled in the above-described manner and reassembled such that lower clamp head 110 is adjacent the tightening bar 136 and the upper clamp head 120 is adjacent to the distal ends 112B, 114B of the first and second post 112, 114. In such assemblies, the tightening bar 136 may be engaged to draw the lower clamp head 110 toward the upper clamp head 120, thereby imposing a compressive force on any coupling ring 300 situated therebetween.

Alternatively, the first end and the second end of the bar 136A may each have a notch therein of sufficient size to receive the first post 112 and the second post 114, respectively, therein. However, one of skill in the art will appreciate that any device suitable for removably securing two objects together may be used to secure the bar 136A to the first post 112 and to the second post 114. In some instances, the bar 136A may have one end with a notch therein while the other end is rotably secured to either the first or second post 112, 114.

The bar 136A has a threaded opening that extends transversely through the bar 136A and is disposed between the first end and the second end of the bar 136A. As shown in FIGS. 1-4 and 14-15, the bolt 136B has threads that are compatible with the threads of the opening in the bar 136A such that the bolt can be threaded transversely through the bar 136A towards the upper clamp head 120. Thus, the bolt 136B moves through the opening as a user applies torque in a defined, tightening motion. Once the bolt 136B contacts the upper clamp head 120, any additional torque applied by a user to the bolt 136B causes the upper clamp head 120 to draw toward the lower clamp head 110. As shown in FIGS. 1-4 and 13-15, the bolt 136B may have a nut secured to one or both of its ends having a diameter greater than the diameter of the opening within the bar 136A to prevent the bolt 136B from passing completely through the opening of the bar 136A. Alternatively, one or both ends of the bolt 136B may have an enlarged head having a diameter greater than the diameter of the opening within the bar 136A to achieve this same end.

As shown in FIGS. 5-9 and 11-12, in another preferred embodiment, the fastener 130 comprises a first nut 132 and a second nut 134. In such embodiments, the first post 112 has a threaded distal end 112B and the second post 114 has a threaded distal end 114B. In a preferred embodiment, the first post 112 and the second post 114 are threaded only on their distal ends 112B, 114B, as shown in FIGS. 4 and 13. Alternatively, the entirety of the first post 112 and the second post 114 may be threaded. The first nut 132 has threading compatible with the threading present on the threaded distal end 112B of the first post 112 such that the first nut 132 may be screwed toward the proximal end 112A of the first post 112. The second nut 134 has threading compatible with the threading present on the threaded distal end 114B of the second post 114 such that the second nut 134 may be screwed toward the proximal end 114A of the second post 114.

As a user applies torque in a defined, tightening direction to the first nut 132 and the second nut 134, the nuts draw towards the proximal end of the first post 112 and the second post 114, respectively. Accordingly, once each nut 132, 134 contacts the topside 120B of the upper clamp head 120, any additional torque applied to the nuts 132, 134 in the defined, tightening motion causes the upper clamp head 120 to draw towards the lower clamp head 110, thereby crimping any coupling ring 300 positioned between the clamp heads. In addition to drawing the upper clamp head 120 towards the lower clamp head 110, the first nut 132 and the second nut 134 may also serve to prevent the upper clamp head 120 from sliding off of the first post 112 and/or second post 114.

To provide a better griping surface for hand or tool, the first nut 132 and the second nut 134 may be a hex nut defined by six faces, though one of skill in the art will appreciate any suitable nut may be used. In one preferred embodiment, the first nut 132 and the second nut 134 are both double-headed nuts each having a first head and a second head separated by a cylindrical body, as shown best in FIGS. 5-9 and 11-13. In a preferred embodiment, the first post 112 and the second post 114 are designed such that the first nut 132 and the second nut 134 may be removed from the first post 112 and the second post 114, respectively. In such embodiments, the upper clamp head 120 may be removed by placing the apparatus 100 in an open configuration, removing the first nut 132, and sliding the upper clamp head 120 off of the first post 112. Alternatively, the first post 112 and second post 114 may be designed such that the first nut 132 and the second nut 134 cannot be removed from the first post 112 and the second post 114, respectively.

As shown in FIGS. 13-15, in yet another preferred embodiment, the fastener 130 may be a combination of the first nut 132, the second nut 134, and the tightening bar 136. In such embodiments, the first end of the bar 136A of the tightening bar 136 is secured to the first nut 132 and the second end of the bar 136B is secured to the second nut 134. In a preferred embodiment, the bar 136A is removably secured to the first and second nut 132, 134. In one such embodiment, the first nut 132 and second nut 134 are preferably double-headed, as described above, and the bar 136A of the tightening bar 136 has notches within its first and second end configured to receive the cylindrical body of the first nut 132 and second nut 134 therein, respectively. Once the cylindrical body of the first nut 132 and the second nut 134 are received within the notches of the bar 136A, the bar 136A may rest upon the first and second nut 132, 134, as shown in FIGS. 14-15. Alternatively, one end of the bar 136A may be permanently secured to the nut to which it corresponds while the other end is removably secured, or both ends may be permanently secured to their respective nuts. In some instances, one end of the bar 136A may be rotably secured to its respective nut.

To accommodate coupling rings 300 having diameters different than the diameter of the opening formed when the apparatus 100 is in a crimped configuration, the apparatus 100 may further comprise an insert 200. As shown best in FIGS. 1-2, 10A-12 and 14-15, the insert 200 comprises a first insert member 210 configured to receive a first portion of a coupling ring 300 therein and a second insert member 220 configured to receive a second portion of a coupling ring 300 therein. The first insert member 210 secures to the lower clamp head 110 and the second insert member 220 secures to the upper clamp head 220. Preferably, the first and second insert members 210, 220 are removably secured to the lower and upper clamp heads 110, 120, respectively.

Figure 10A:
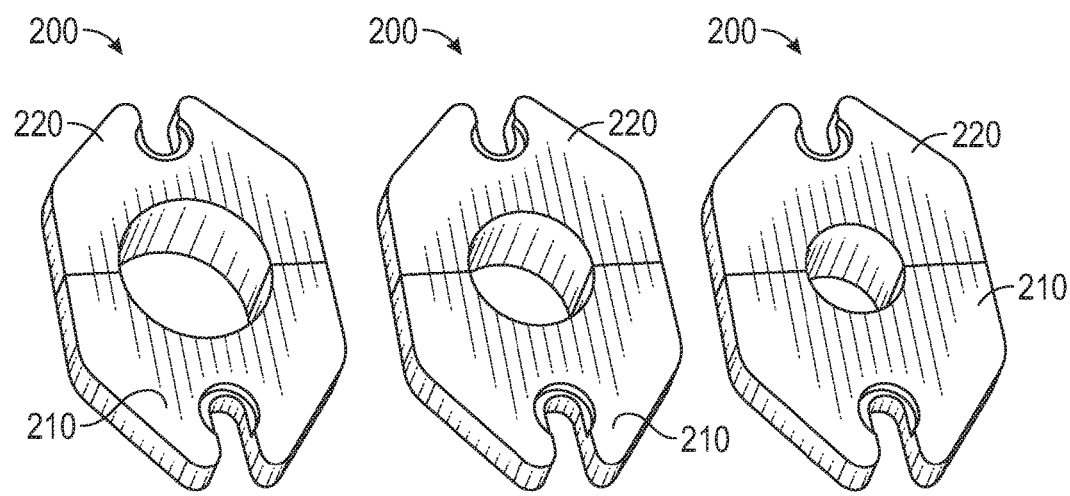
FIG. 10A shows a front perspective view of three separate inserts embodying features consistent with the principles of the present disclosure.
Figure 10B:
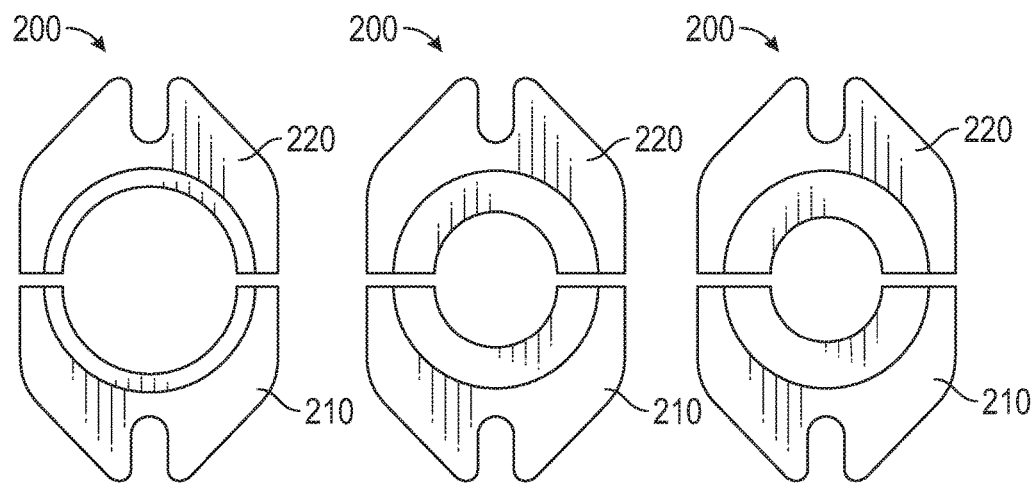
FIG. 10B shows a rear elevational view of a three separate inserts embodying features consistent with the principles of the present disclosure.
Figure 11:
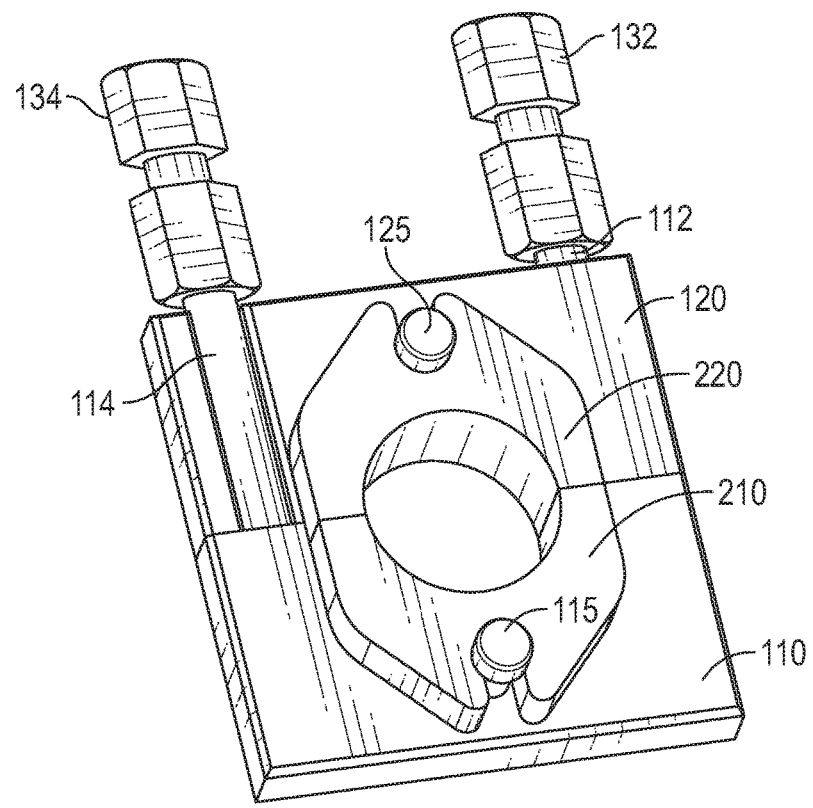
FIG. 11 shows a perspective view of an apparatus embodying features consistent with the principles of the present disclosure.

When the first and second insert members 210, 220 are secured to the lower and upper clamp heads 110, 120, respectively, and the apparatus 100 is placed in a crimped configuration, the opening formed by the insert members has a smaller diameter than the opening formed by the clamp heads, as shown best in FIG. 14. In this way, the insert 200 may be used to crimp smaller coupling rings 300 than what is possible with the lower clamp head 110 and upper clamp head 120 alone. In a preferred embodiment, the first insert member 210 and the second insert member 220 each have a semicircular arch therein, such that when the apparatus 100 is placed in a crimped configuration, the opening formed by the first insert member 210 and the second insert member 220 is circular. FIGS. 10A-10B illustrate that the insert 200 may be shaped or sized to accommodate coupling rings 300 of various sizes including, but not limited to, couplings rings 300 having a one inch, three-quarters inch, five-eights inch, or three-eights inch diameter. In a preferred embodiment, the first insert member 210 and the second insert member 220 may each have a notch therein configured to receive a portion of a stepped rod therein, as disclosed below. As shown in FIGS. 12 and 15, the notch within the first insert member 210 is preferably opposite of the portion of the first insert member 210 configured to receive a first portion of a coupling ring 300 ring therein. The notch within the second insert member 220 is preferably opposite of the portion of the second insert member 220 configured to receive a second portion of a coupling ring 300 therein.

To facilitate quick removal of the first and second insert members 210, 220, the lower clamp head 110 may have a first quick release mechanism 115, and the upper clamp head 120 may have a second quick release mechanism 125, as shown in FIGS. 1-9, 11-12, and 14-15. The first quick release mechanism 115 is configured to removably secure the first insert member 210 to the lower clamp head 110, and the second quick release mechanism 125 is configured to removably secure the second insert member 220 to the upper clamp head 120. To accommodate the first and second quick release mechanisms 115, 125, the lower clamp head 110 and the upper clamp head 120 may each have an opening that extends through the clamp head from the front face 110E, 120E to the back face 110F, 120F, respectively.

Both the first and second quick release mechanisms 115, 125 are spring-loaded release systems each comprising a spring and a stepped rod. The stepped rod of each quick release mechanism 115, 125 extends through the opening extending through the front face 110E, 120E to the back face 110F, 120F of the lower and upper clamp heads 110, 120, respectively. The stepped rod of each quick release mechanism 115, 125 comprises a front face piece and a back face piece. The back face piece comprises a rod having an enlarged end and a male connector end opposite the enlarged end. The front face piece comprises a rod having an enlarged end and a female connector end opposite the enlarged end. The back face piece of the first and second quick release mechanism 115, 125 are inserted into the opening of the lower and upper clamp heads 110, 120, respectively, such that the enlarged end of the back face piece is disposed above the back face 110F, 120F of the clamp heads 110, 120. The front face piece of the first and second quick release mechanism 115, 125 is inserted into the opening of the lower and upper clamp head 110, 120, respectively, such that the enlarged end of the front face piece is disposed above the front face 110E, 120E of the clamp heads 110, 120. The male end of the back face piece fits inside the female end of the front face piece such that the two pieces are generally inseparable once joined, thereby forming the stepped rod. The enlarged end of the front face piece and the enlarged end of the back face piece prevent the stepped rod from falling out of the lower and upper clamp heads 110, 120, respectively.

Figure 9:
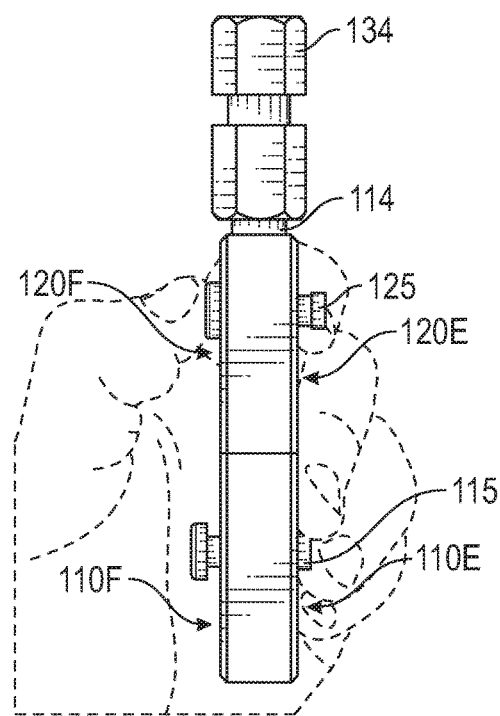
FIG. 9 shows a side elevational view of an apparatus embodying features consistent with the principles of the present disclosure.

The spring of the first and second release mechanisms 115, 125 is inserted into the opening extending through the front face to the back face of each clamp head prior to the front face piece and back face piece being permanently fit together. The spring of each quick release mechanism 115, 125 exerts a force that causes the stepped rod of each quick release mechanism 115, 125 to be biased in one direction. In a preferred embodiment, as shown best in FIG. 8, each spring is biased such that the enlarged end of the front face piece of each stepped rod is pressed against the front face 110E, 120E of each clamp head 110, 120. As shown in FIG. 9, a user may press the enlarged end of each of the back face pieces towards the back face 110F, 120F of each clamp head 110, 120 to draw the enlarged end of each of the front face pieces away from the front face 110E, 120E, thereby causing a portion of the rod of the front face piece to be exposed. While exposed, the notch within an insert member 210, 220 may be positioned around the portion of the rod exposed. Once the insert member 210, 220 is in place, the user may release the back face piece of the stepped rod. Once force is removed from the back face piece, the front face piece draws back towards the front face of the clamp head to which it is biased, thereby securing the insert member to the clamp head, as shown in FIGS. 1-2, 11-12 and 14-15. Although the use of quick release mechanisms is generally preferred, it is understood that the any instrument or device suitable for removably securing two objects together may be used to secure the first insert member 210 and the second insert member 220 to the lower clamp head 110 and upper clamp head 120, respectively.

Because significant force may be imposed on the apparatus 100, it is preferred that the structural elements of the apparatus 100 be constructed of metal. However, one of skill in the art will readily appreciate that other materials may be used, including, but not limited to, wood, plastic, rubber, stone, or any other suitable material, without departing from the inventive subject matter disclosed herein. The structural elements of the apparatus 100 may all be made of the same type of material or of different materials.

In another aspect, the present disclosure is directed toward a method for crimping a coupling ring 300 using the apparatus 100 of the present disclosure. To use the apparatus 100 to crimp a coupling ring 300, the lower clamp head 110 is first positioned around a first portion of the coupling ring 300. Once the lower clamp head 110 is in position, the upper clamp head 120 is rotated about the first post 112 until the indentation 122 within the upper clamp head 120 receives the second post 114 therein, thereby placing the apparatus 100 in a closed configuration. In some instances, the upper clamp head 120 may need to be lifted or slid up towards the distal end 112B of the first post 112 in the manner disclosed above prior to placing the apparatus 100 in a closed configuration. Once the apparatus 100 is placed in a closed configuration, the upper clamp head 120 may rest on top of the second portion of the coupling ring 300. The fastener 130 is subsequently engaged to draw the upper clamp head 120 toward the lower clamp head 110 such that the clamp heads are engaged with and applying compressive forces to the coupling ring 300, thereby causing the coupling ring 300 to crimp.

In instances where a user has switched the positioning of lower clamp head 110 and upper clamp head 120, i.e., where the lower clamp head 110 is adjacent the fastener 130 and the upper clamp head 120 is adjacent the proximal ends 112A, 114A of the first and second posts 112, 114, respectively, an alternative methodology may be carried out. In such methodologies, the upper clamp head 120 is rotated until the apparatus 100 retains a closed configuration. The upper clamp head 120 is then positioned around a first portion of the coupling ring 300. In some instances the lower clamp head 110 may need to be lifted or slid up toward the distal ends 112B, 114B of the first and second post 112, 114, respectively, prior to positioning the upper clamp head 120 around the coupling ring 300. Once the upper clamp head 120 is positioned around the first portion of the coupling ring 300, the lower clamp head 110 may rest on top of the second portion of the coupling ring 300. The fastener 130 is subsequently engaged to draw the lower clamp head 110 toward the upper clamp head 120 such that the clamp heads are engaged with and applying compressive forces to the coupling ring 300, thereby causing the coupling ring 300 to crimp.

In a preferred methodology, the step of engaging the fastener 130 may involve engaging the bolt 136B of the tightening bar 136 by rotating the bolt 136B in a defined, tightening motion. In another preferred methodology, the step of engaging the fastener 130 may involve screwing the first nut 132 toward the proximal end 112A of the first post 112 and screwing the second nut 134 toward the proximal end 114A of the second post 114. In some instances, the methodology disclosed herein may further comprise the steps of securing the first insert member 210 to the lower clamp head 110 and securing the second insert member 220 to the upper clamp head 120.

As shown best in FIGS. 12 and 15, the apparatus 100 and method disclosed herein may be used to secure a coupling ring 300 around flexible piping 400. However, one of skill in the art will appreciate that the apparatus 100 and method disclosed herein may be utilized in other environments or applications without departing from the inventive subject matter disclosed herein.

It is understood that versions of the inventive subject matter of the present disclosure may come in different forms and embodiments. Additionally, it is understood that one of skill in the art would appreciate these various forms and embodiments as falling within the scope of the inventive subject matter disclosed herein.

What is claimed is:

1. A crimping apparatus, comprising:
 a first post;
 a second post;
 a lower clamp head configured to receive a first portion of a coupling ring therein, wherein the lower clamp head is slidably secured to the first post and the second post;
 an upper clamp head configured to receive a second portion of the coupling ring therein, wherein the upper clamp head is rotably secured to the first post, the upper clamp head has an indentation configured to receive the second post therein, and the lower clamp head and the upper clamp head each have a semicircular arch therein; and
 a fastener configured to draw the upper clamp head toward the lower clamp head.

2. The apparatus of claim 1, wherein the fastener is a tightening bar comprising:
 a bar having a first end removably secured to the first post, a second end removably secured to the second post, and a threaded opening disposed between the first end and the second end and extending transversely through the bar; and
 a bolt configured to draw the upper clamp head toward the lower clamp head when the bolt is threaded through the threaded opening in the bar.

3. The apparatus of claim 2, wherein the first post and the second post each have an enlarged proximal end and a threaded distal end, and wherein the first end of the bar has a first bore therein and the second end of the bar has a second bore therein, the first bore having threading compatible with the threaded distal end of the first post such that the distal end of the first post can be screwed into the first bore, and the second bore having threading compatible with the threaded distal end of the second post such that the distal end of the second post can be screwed into the second bore.

4. The apparatus of claim 1, wherein the upper clamp head has a bottom side, a top side, and a bore extending from the bottom side to the top side of the upper clamp head such that the bore has an opening at the bottom side and at the top side of the upper clamp head.

5. The apparatus of claim 1, wherein the lower clamp head has a bottom side, a top side, a first bore extending from the bottom side to the top side of the lower clamp head such that the first bore has an opening at the bottom side and at the top side of the lower clamp head, and a second bore parallel to the first bore and extending from the bottom side to the top side of the lower clamp head such that the second bore has an opening at the bottom side and at the top side of the lower clamp head.

6. The apparatus of claim 1, further comprising an insert, wherein the insert comprises:
   a first insert member removably secured to the lower clamp head, wherein the first insert member is configured to receive the first portion of the coupling ring therein; and
   a second insert member removably secured to the upper clamp head, wherein the second insert member is configured to receive the second portion of the coupling ring therein.

7. The apparatus of claim 6, wherein the lower clamp head has a first quick release mechanism configured to secure the first insert member to the lower clamp head, and the upper clamp head has a second quick release mechanism configured to secure the second insert member to the upper clamp head.

8. A crimping apparatus comprising:
   a first post;
   a second post;
   a lower clamp head configured to receive a first portion of a coupling ring therein, wherein the lower clamp head has a bottom side, a top side, a first bore extending from the bottom side to the top side of the lower clamp head such that the first bore has an opening at the bottom side and at the top side of the lower clamp head, and a second bore parallel to the first bore and extending from the bottom side to the top side of the lower clamp head such that the first bore has an opening at the bottom side and at the top side of the lower clamp head, the lower clamp head being slidably secured to the first post when the first post is inserted through the first bore and being slidably secured to the second post when the second post is inserted through the second bore;
   an upper clamp head configured to receive a second portion of the coupling ring therein, wherein the upper clamp head has a bottom side, a top side, an indentation extending front the bottom side to the top side configured to receive the second post therein, and a third bore extending from the bottom side to the top side such that the third bore has an opening at the bottom side and at the top side of the upper clamp head, the lower clamp head and the upper clamp head each having a semicircular arch therein and the upper clamp head being rotably secured to the first post when the first post is inserted through the third bore; and
   a fastener comprising:
      a bar having a first end removably secured to the first post, a second end removably secured to the second post, and an opening disposed between the first end and the second end extending transversely through the bar; and
      a bolt configured to draw the upper clamp head toward the lower clamp head when the bolt is threaded through the opening in the bar.

9. The apparatus of claim 8, wherein the first post and the second post each have an enlarged proximal end and a threaded distal end, and wherein the first end of the bar has a fourth bore therein and the second end of the bar has a fifth bore therein, the fourth bore having threading compatible with the threaded distal end of the first post such that the distal end of the first post can be screwed into the fourth bore, and the fifth bore having threading compatible with the distal end of the second post such that the distal end of the second post can be screwed into the fifth bore.

10. The apparatus of claim 8 further comprising an insert, wherein the insert comprises:
    a first insert member removably secured to the lower clamp head, wherein the first insert member is configured to receive the first portion of the coupling ring therein; and
    a second insert member removably secured to the upper clamp head, wherein the second insert member is configured to receive the second portion of the coupling ring therein.

11. The apparatus of claim 10, wherein the lower clamp head has a first quick release mechanism configured to secure the first insert member to the lower clamp head, and the upper clamp head has a second quick release mechanism configured to secure the second insert member to the upper clamp head.

12. A crimping apparatus, comprising:
    a lower clamp head configured to receive a first portion of a coupling ring therein, wherein the lower clamp head has a first post and a second post extending therefrom;
    an upper clamp head configured to receive a second portion of the coupling ring therein, wherein the upper clamp head is rotably secured to the first post, the upper clamp head has an indentation configured to receive the second post therein, and the lower clamp head and the upper clamp head each have a semicircular arch therein; and
    a fastener configured to draw the upper clamp head toward the lower clamp head.

13. The apparatus of claim 12, wherein the first post and the second post each have a proximal end and a threaded distal end, and wherein the fastener comprises a first nut and a second nut,
    the first nut having threading compatible with the threaded distal end of the first post such that the first nut can be screwed toward the proximal end of the first post, and the second nut having threading compatible with the threaded distal end of the second post such that the second nut can be screwed toward the proximal end of the second post.

14. The apparatus of claim 13 further comprising a tightening bar, wherein the tightening bar comprises:
    a bar having a first end secured to the first nut, a second end secured to the second nut, and an opening disposed between the first end and the second end extending transversely through the bar; and
    a bolt configured to draw the upper clamp head toward the lower clamp head when the bolt is threaded through the opening in the bar.

15. The apparatus of claim 12, wherein the fastener is a tightening bar comprising:
    a bar having a first end secured to the first post, a second end secured to the second post, and an opening disposed between the first end and the second end and extending transversely through the bar; and
    a bolt configured to draw the upper clamp head toward the lower clamp head when the bolt is threaded through the opening in the bar.

16. The apparatus of claim 12, wherein the upper clamp head has a bottom side, a top side, and a bore extending from the bottom side to the top side such that the bore has an opening at the bottom side and at the top side of the upper clamp head.

17. The apparatus of claim 12, further comprising an insert, wherein the insert comprises:

a first insert member removably secured to the lower clamp head, wherein the first insert member is configured to receive the first portion of the coupling ring therein; and a second insert member removably secured to the upper clamp head, wherein the second insert member is configured to receive the second portion of the coupling ring therein.

18. The apparatus of claim 17, wherein the lower clamp head has a first quick release mechanism configured to secure the first insert member to the lower clamp head, and the upper clamp head has a second quick release mechanism configured to secure the second insert member to the upper clamp head.

* * * * *